(12) United States Patent
Hong

(10) Patent No.: US 10,640,436 B2
(45) Date of Patent: May 5, 2020

(54) PRODUCTION OF AROMATIC HYDROCARBONS FROM LIGHT ALKANES

(71) Applicant: Kainos Tech Incorporated, Crown Point, IN (US)

(72) Inventor: Jin Ki Hong, Cypress, CA (US)

(73) Assignee: KAINOS TECH INCORPORATED, Crown Point, IN (US)

( * ) Notice: Subject to any disclaimer, the term of this patent is extended or adjusted under 35 U.S.C. 154(b) by 0 days.

(21) Appl. No.: 15/858,734

(22) Filed: Dec. 29, 2017

(65) Prior Publication Data

US 2018/0354873 A1    Dec. 13, 2018

Related U.S. Application Data

(60) Provisional application No. 62/603,837, filed on Jun. 13, 2017.

(51) Int. Cl.
| | | |
|---|---|---|
| *C07C 6/12* | (2006.01) |
| *B01J 8/22* | (2006.01) |
| *B01J 8/18* | (2006.01) |
| *C07C 15/02* | (2006.01) |
| *C07C 9/04* | (2006.01) |
| *B01J 8/00* | (2006.01) |
| *B01J 8/26* | (2006.01) |

(52) U.S. Cl.
CPC ............... *C07C 6/12* (2013.01); *B01J 8/0055* (2013.01); *B01J 8/1836* (2013.01); *B01J 8/1872* (2013.01); *B01J 8/22* (2013.01); *B01J 8/26* (2013.01); *C07C 9/04* (2013.01); *C07C 15/02* (2013.01); *B01J 2208/00991* (2013.01); *C10G 2300/1081* (2013.01); *C10G 2400/20* (2013.01); *C10G 2400/26* (2013.01); *C10G 2400/30* (2013.01)

(58) Field of Classification Search
CPC ........... C07C 6/12; C07C 2/72; B01J 19/0046
USPC .................................................. 585/322, 407
See application file for complete search history.

(56) References Cited

U.S. PATENT DOCUMENTS

| | | | |
|---|---|---|---|
| 5,053,570 A | 10/1991 | Soto et al. | |
| 2012/0029256 A1* | 2/2012 | Chen ........................ | C07C 2/76 585/407 |
| 2016/0289141 A1* | 10/2016 | Bachmann .............. | C07C 5/367 |

FOREIGN PATENT DOCUMENTS

GB            1147359 A  *   4/1969   ............ B01J 8/1836

* cited by examiner

*Primary Examiner* — In Suk C Bullock
*Assistant Examiner* — Jason Y Chong
(74) *Attorney, Agent, or Firm* — STIP Law Group, LLC

(57) ABSTRACT

Provided is a method for producing aromatic hydrocarbons from light alkanes. A light alkane feed is contacted with catalyst particles in each of reactors, wherein each of the reactors is a fluidized bed reactor and arranged in parallel with each other in a furnace. At least a portion of the alkane feed is converted to aromatic hydrocarbons using the catalyst particles, wherein the aromatic hydrocarbons form a part of a reactor effluent stream. The reactor effluent streams from each of the reactors are merged to form a first merged effluent stream. The first merged effluent stream is separated into the aromatic hydrocarbons, light hydrocarbons, and a fuel gas.

13 Claims, 4 Drawing Sheets

PRODUCTION OF AROMATIC HYDROCARBONS FROM LIGHT ALKANES

CROSS-REFERENCE TO RELATED APPLICATIONS

This application claims the benefit of priority under 35 U.S.C. § 119(e) to U.S. Provisional Patent Application No. 62/603,837, filed on Jun. 13, 2017, which is hereby incorporated by reference in its entirety.

FIELD OF INVENTION

The present invention relates to a process and an apparatus for producing aromatic hydrocarbons from a light alkane feed.

BACKGROUND OF THE INVENTION

A stable supply of light alkane feedstock at large volumes enabled by shale gas production incentivizes new chemical process development for key petrochemicals production. Aromatic hydrocarbons such as benzene, toluene, and xylenes are derived from crude oil through catalytic reforming of straight-run heavy naphtha and steam cracking of light naphtha. Driven by geopolitical instabilities in crude oil production regions, production and supply of crude oil has been unpredictable, and its volatile market price has reached unaffordable levels in short period of times. Therefore, a need for cost-advantaged feedstock with a stable supply has been growing for production of aromatic hydrocarbons.

Aromatic hydrocarbon production from light alkanes offers incentives including an abundant and stable supply of feedstock at competitive prices. Light alkanes can undergo catalytic reactions including dehydrogenation, oligomerization, and cyclization in a complex manner until aromatic hydrocarbons are produced. Measurable quantities of hydrogen, methane, light alkanes other than feed alkane, and light alkenes (or light olefins) are also produced as byproducts. Even though light alkanes offer economic incentives as a new feedstock, there remain technical obstacles for industrial scale production of aromatic hydrocarbons from light alkanes.

Light alkane conversion to aromatic hydrocarbons is a strongly endothermic reaction and, therefore, the process for producing aromatic hydrocarbons from light alkanes requires supplying a large quantity of reaction heat. Approximately 4,399 kJ of thermal energy is required for the reaction heat per kg of benzene produced from ethane. The dehydrogenation step of the light alkane feed is mainly responsible for the reaction heat requirement. Considering the strong endothermic requirement, there needs to be a reliable and efficient method and apparatus for providing reaction heat required for producing aromatic hydrocarbons from light alkanes at an industrially attractive production rate.

The present invention found that another important factor in aromatic hydrocarbon production is uniform catalyst bed temperature in a specific temperature range. Findings of the present invention suggest that light alkane conversion for aromatic hydrocarbons production is highly sensitive to reaction temperature in terms of light alkane conversion rate and catalyst deactivation. If the catalyst bed temperature is below 500° C., light alkane conversion rate is too low to meet commercially attractive production rates. On the other hand, unacceptably fast catalyst deactivation is driven at catalyst bed temperatures higher than 660° C., and renders a catalyst cycle time that is too short between catalyst regenerations for commercial operation. Achieving a uniform catalyst bed temperature in a desired temperature range, preferably between 500° C. and 660° C., more preferably between 520° C. and 640° C., and most preferably between 540° C. and 620° C., in industrial scale reactors is critical for commercial viability of aromatic hydrocarbons production from light alkanes.

Methods for supplying reaction heat have been developed by chemical industry for reactions of an endothermic nature. However, adoption of these methods for aromatic hydrocarbon production from light alkane feedstock yields undesirable operational issues and non-uniform temperature distribution in the catalyst bed. For instance, preheating light alkane feedstock to provide sufficient sensible heat for the endothermic reaction is not feasible because the reaction heat required for industrially attractive rates is substantially larger than the quantity of sensible heat achievable through feedstock preheating. Excessive preheating of the feedstock in an attempt to increase sensible heat and provide the reaction heat required often leads to technical issues, including thermal breakdown of feedstock, accelerated catalyst deactivation, and shortened lifetime of preheating tubes. Heating an inter-stage stream for the next stage reactor in a serially connected multi-stage reactors configuration is not practical either because heating of the inter-stage stream leads to thermal breakdown of the desired product at elevated temperatures and resultant building-up of coke inside the tube.

Intensive heating-up of reactor tubes with a fixed catalyst bed would not be applicable. Catalyst with a fixed position in a stationary state inside an externally heated reactor impedes heat supply itself, and creates non-uniform temperature distribution within the catalyst bed. This leads to accelerated catalyst coking, catalyst sintering problems near the reactor wall, not enough thermal energy to drive the endothermic reaction in the center of the catalyst bed.

Catalyst heating by burning coke while regenerating catalyst (and burning extra fuel when needed) and recycling heated catalyst for reaction heat supply has been explored. Even though circulation of heated catalyst particles from the catalyst regenerator for reaction heat supply has been commercially employed in fluid catalytic cracking (FCC) for heavy portions of crude oil, the same approach would not work properly with light alkanes as feedstock. Light alkane conversion for production of aromatics requires substantially larger amounts of reaction heat than cracking of heavy portions of crude oil when compared on a per unit feedstock mass basis. The present invention also found that light alkane feed produces coke at substantially lower yields than FCC for heavy portions of crude oil. The much stronger endothermic requirement of light alkane feed combined with the substantially lower coke yield makes it impractical to use coke as source of reaction heat supply.

Catalyst deactivation driven by coke formation is another technical hurdle in aromatic hydrocarbon production from light alkanes. Formation of coke over or within the catalyst structure progresses over the course of aromatic hydrocarbon production, leading to a gradual drop in aromatic hydrocarbon production rates. Regeneration of deactivated catalysts makes it difficult or impossible to produce aromatic hydrocarbons from a reactor in a continuous manner and to operate downstream separation units without interruption.

Taken together, there is a need for a new process and apparatus for producing aromatic hydrocarbons from a feedstock of light alkanes by developing a reliable and efficient reaction heat supply to the reactor with uniform catalyst bed temperature in a desired temperature range and by making the entire process continuous.

SUMMARY OF THE INVENTION

A new process and apparatus for producing aromatic hydrocarbons from light alkane feedstock is provided. The process comprises contacting a light alkane feed with catalyst particles in each of reactors, wherein each of the reactors is a fluidized bed reactor and arranged in parallel with each other in a furnace; converting at least a portion of the alkane feed to aromatic hydrocarbons using the catalyst particles, wherein the aromatic hydrocarbons form a part of a reactor effluent stream; merging the reactor effluent streams from each of the reactors to form a first merged effluent stream; and separating the first merged effluent stream into the aromatic hydrocarbons, light hydrocarbons, and a fuel gas. The aromatic hydrocarbons are benzene, toluene, xylenes, or a combination thereof. The light alkane feed may comprise ethane, propane, butane, or a combination thereof. The fuel gas comprises methane and hydrogen. The light hydrocarbons may comprise alkanes and alkenes from $C_2$ to $C_4$. Each of the reactors fluidizes and circulates the catalyst particles inside the reactor. The catalyst particles may be 10-500 micrometers in diameter.

In the converting step, an outside wall of each of the reactors is heated by a flue gas, wherein the flue gas is generated by combustion of a gaseous fuel or a liquid fuel. The pressure of the reactor is 200 psig (1,480 kPa) or less. The temperature of the catalyst particles is between 500° C. and 660° C. during the converting step. The temperature of the furnace is between 700° C. and 1200° C. during the converting step. An end portion of each of the reactors is protruded from a wall of the furnace, wherein the protruded portion is 0%-70% of the length of each of the reactors in a height direction.

The process may further comprise a step of regenerating the catalyst particles to reactivate the catalyst particles deactivated during the converting step, wherein the reactors are fluidly disconnected from the light alkane feed and fed with a gas stream containing either air or hydrogen during the regenerating step.

Reactors in a furnace may be switched between in a production mode for producing aromatic hydrocarbons and in a regeneration mode for regenerating catalysts deactivated during the production mode.

In one embodiment, the furnace comprises multiple furnaces, and the first merged effluent stream from each of the multiple furnaces is further merged with each other to form a second merged effluent stream. The process may comprise a step of regenerating the catalyst particles to reactivate the catalyst particles deactivated during the converting step, wherein the reactors in the furnace in which the regenerating step occurs are fluidly disconnected from the light alkane feed and fed with a gas stream containing either air or hydrogen during the regenerating step. The reactors in the furnace in which the regenerating step occurs may be fluidly disconnected from the second merged effluent stream.

DETAILED DESCRIPTION OF THE INVENTION

Figure 1:
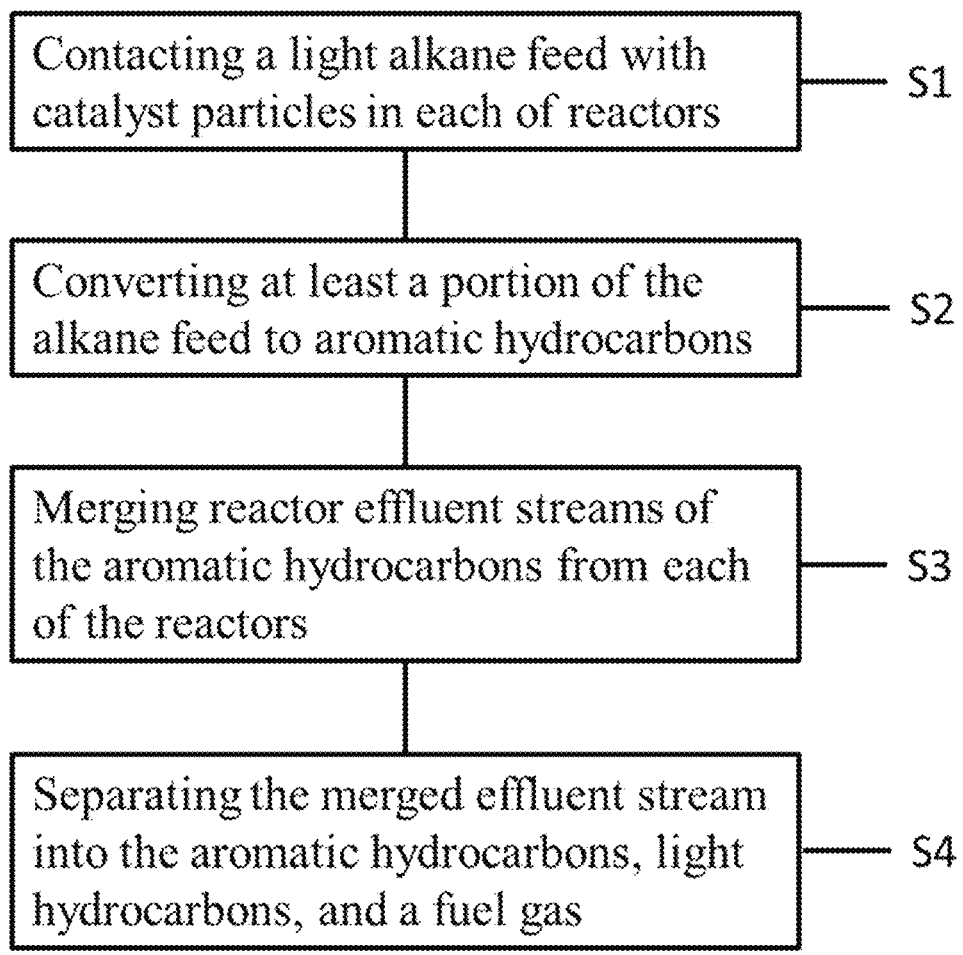
FIG. 1 shows the steps of producing aromatic hydrocarbons from a light alkane feed.

FIG. 1 shows a process for producing aromatic hydrocarbons which comprises contacting a light alkane feed with catalyst particles in each of the reactors (S1), converting at least a portion of the alkane feed to aromatic hydrocarbons (S2), merging reactor effluent streams from each of the reactors (S3), and separating the merged effluent stream into the aromatic hydrocarbons, light hydrocarbons, and a fuel gas (S4). The aromatic hydrocarbons are benzene, toluene, xylenes, or a combination thereof. The light alkane feedstock comprises ethane, propane, butane or any combination thereof. Light alkane is also referred to as lower alkane or light or lower paraffin.

Figure 2:
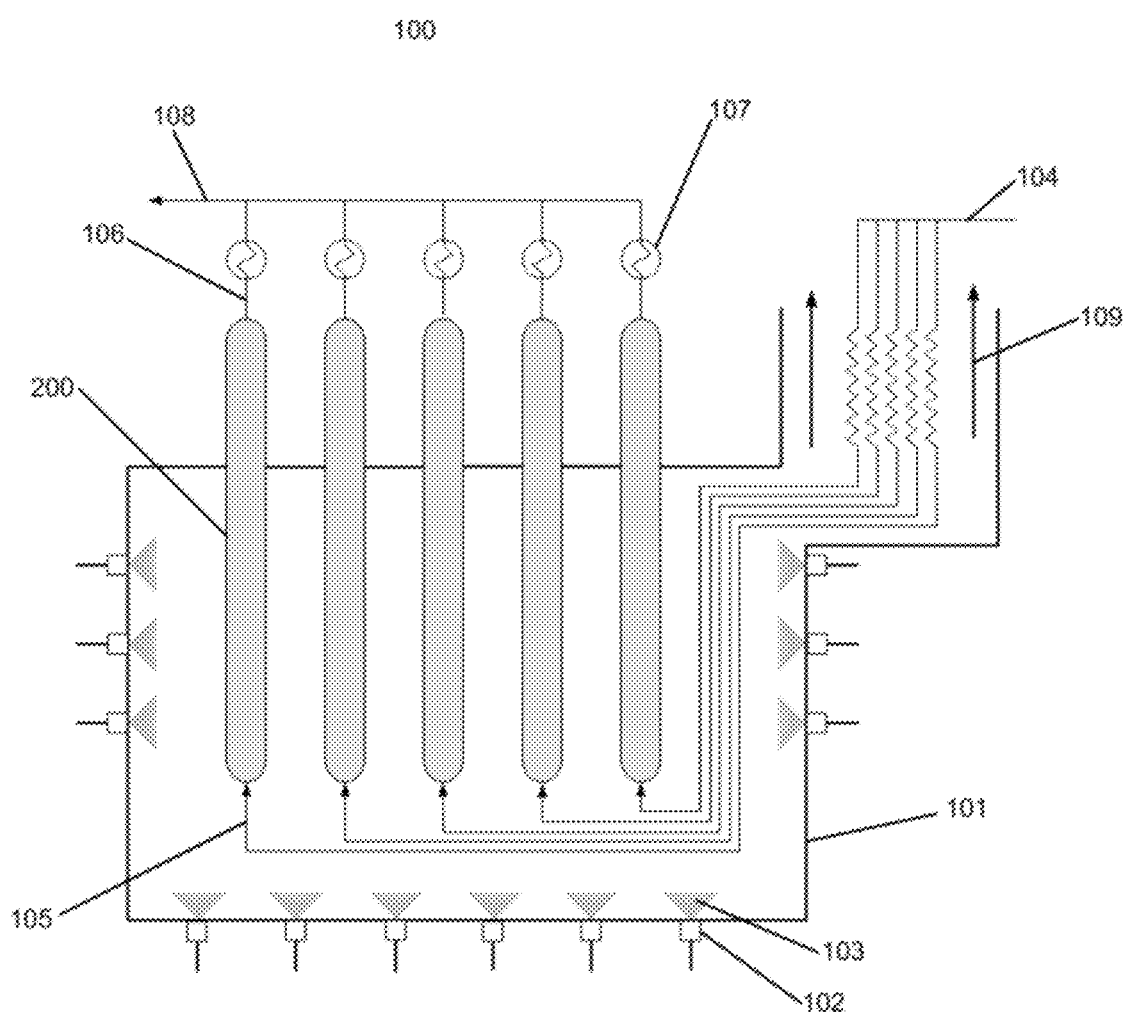
FIG. 2 is a simplified schematic diagram of a furnace of the present invention in which multiple fluidized bed reactors are arranged in parallel, and the reactors are heated by flue gas for aromatic hydrocarbon production.

FIG. 2 shows a simplified schematic diagram of a furnace 100 of the present invention in which multiple reactors 200 are heated by flue gas for aromatic hydrocarbon production. The reactors are fluidized bed reactors. The reactors are arranged in parallel with each other in a furnace 101. The number of reactors varies depending on target production rate and production rates of individual reactors. An end portion of each of the reactors may be protruded from a wall of the furnace, wherein the protruded portion may be 0%-70% of the length of each of the reactors in a height direction. On an inner wall area including a floor or a ceiling of the furnace, multiple burners 102 are installed, and the burners produce a flue gas 103 by combusting a gaseous or a liquid fuel. The burners 102 are positioned in such a way that promotes uniform distribution of thermal energy by the flue gas flow inside the furnace and avoids formation of hot spots on the reactor wall. The light alkane feed 104 is split into multiple streams which are fed into individual reactor 105. Reactor effluent 106 is quenched through a heat exchanger 107. The heat exchanger generates a steam at an elevated pressure (not shown in the diagram) and the steam can be used to meet the process energy requirement. After the heat exchanger 107, reactor effluents 106 from individual reactors are merged to become a first merged effluent stream 108. In one embodiment, quenching of the reactor effluent using a heat exchanger can be done after the reactor effluents are merged. The furnace temperature or flue gas temperature inside the furnace is preferably between 700° C. and 1200° C., more preferably between 750° C. and 1150° C., and most preferably between 800° C. and 1100° C., providing temperature gradients high enough for the heat supply needed for aromatic hydrocarbon production at industrially attractive rates. Flue gas flowing around the outer walls of the reactors in forced convection mechanism promotes heat transfer from the flue gas to the outer walls of the reactor. A heat transfer coefficient higher than 200 W/m²-K is achievable, and realizes aromatic hydrocarbon production at industrially attractive rates. Flue gas before exiting the furnace 109 provides thermal energy for preheating the light alkane feed into the individual reactor 105 and improves efficiency of the process. In order to improve heat exchange from the flue gas to the light alkane feed stream, tubing for the light alkane feed may be manufactured in the form of coils or other shapes so that the contact between the flue gas and the tubing wall is increased.

The fluidized bed reactors in a furnace may be switched between in a production mode for producing aromatic hydrocarbons and in a regeneration mode for regenerating catalysts deactivated during the production mode. The reactors are switched to the regeneration mode as a group when the aromatic hydrocarbon production rate drops below a predetermined rate. Formation of coke over or within the catalyst structure progresses over the course of aromatic hydrocarbon production and this leads to gradual drop in the aromatic hydrocarbon production rate. Controlled coke burning using air or coke conversion to methane gas by reaction with hydrogen proceeds as the light alkane feed is switched to air or hydrogen flow. When catalyst regeneration is completed, the reactors are switched back to light alkane feed for aromatic hydrocarbon production mode operation.

Figure 3:
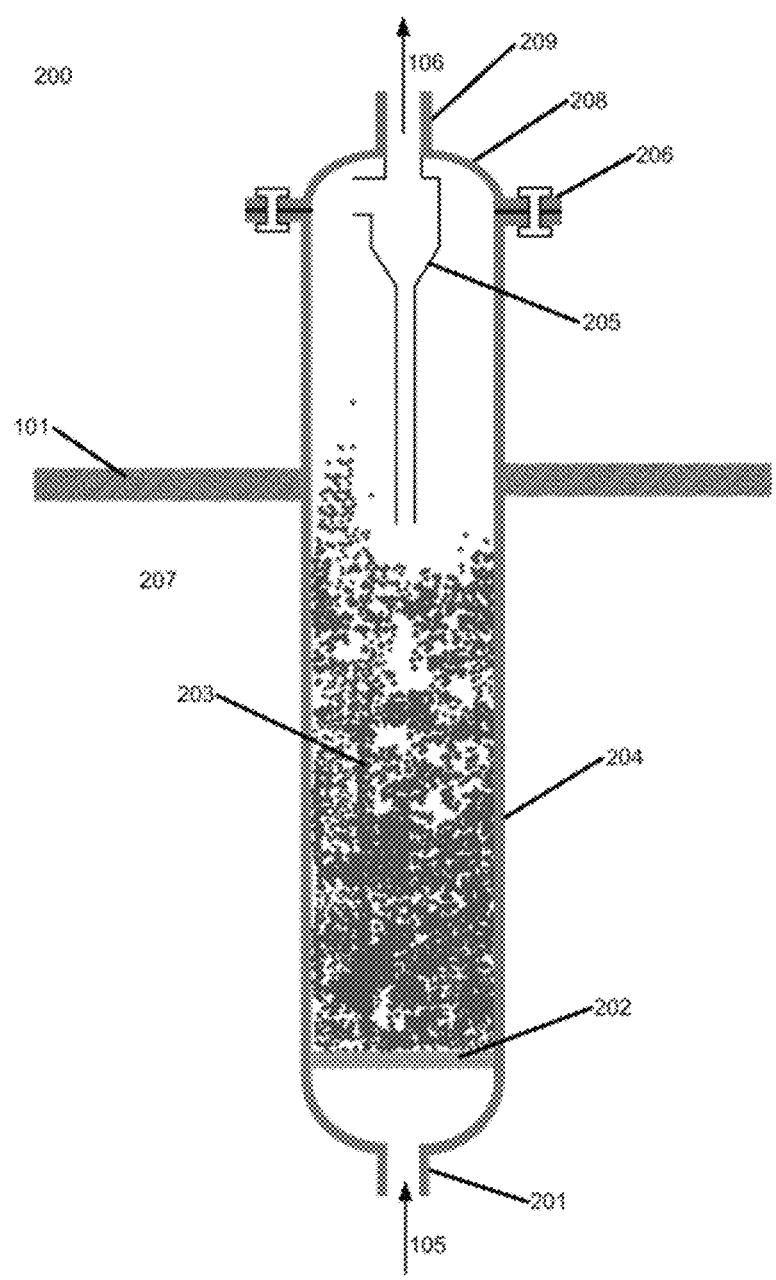
FIG. 3 is a simplified schematic diagram of a fluidized bed reactor of the present invention.

FIG. 3 shows a simplified schematic diagram of a fluidized bed reactor (cross-sectional view) of the present invention. The light alkane feed into the individual reactor 105 enters a fluidized bed reactor 200 through reactor feed inlet 201. The fluidization plate 202 promotes fluidization of catalyst particles (or bed) 203. The catalyst particles comprise bi-functional catalysts and a binder material. The bi-functional catalyst further comprises a dehydrogenation catalyst and an acid catalyst. The dehydrogenation catalyst further comprises a noble metal or a non-noble metal or combination thereof. The acid catalyst comprises a zeolite material with acidity and controlled pore size. Examples include ZSM-5, ZSM-11, ZSM-23, ZSM-35 and ZSM-48. The binder material holds individual catalyst powders together to make a spherical shape of controlled particle sizes, and improves mechanical strength or attrition resistance of the catalyst particles. The binder is thoroughly mixed with metal-loaded zeolite powder before being transferred to spray drying or other mechanical operation for particles formation. The finished catalyst particles are 10-500 micrometers (or microns) in diameter. The fluidization plate 202 may take the form of porous metal plate/disk, bubble cap plates, or spargers. The gas flow rate is regulated for fluidization regimes of either bubbling or turbulent fluidization, or in between the two. Flow rates lower than dense bed transition velocity or higher than transport velocity is not desirable for the present invention.

Thermal energy is transferred from the flue gas to the catalyst particles (or bed) 203 and the gas flow inside the reactor vessel 207 through the reactor wall 204. An end portion of each of the reactors is protruded from a wall of the furnace, wherein the protruded portion is 0%-70% of the length of the reactors in a height direction. The length of the reactor is defined as the length between the uppermost of a reactor feed inlet 201 and the lowermost of a reactor effluent outlet 209. The protruded portion is adjusted so that a reactor portion corresponding to the fluidized catalyst bed is heated by the flue gas inside the furnace, while heating of a portion above the catalyst bed is avoided to minimize thermal breakdown of hydrocarbons.

A cyclone with dipleg 205 separates catalyst particles from gas stream leaving the reactor and returns them to the reactor vessel 207. This minimizes or avoids entrainment of the catalyst particles 203 out of the reactor 200. Multiple cyclones may be connected in series for improved separation of catalyst particles. The cyclone may be installed either internally or externally to the reactor. A flange connection 206 provides gas tight mechanical seal between the reactor vessel 207 and the reactor vessel cover 208. A reactor effluent 106 leaves the reactor 200 through a reactor effluent outlet 209.

Upward flow of the light alkane feed inside the reactor drives fluidization of the catalyst particles and promotes heat transfer from inner surface of the reactor wall to the catalyst particles and gas flow inside the reactor. Driven by the fluid-like behavior of the catalyst particles, a heat transfer coefficient as high as 600 $W/m^2$-K is readily achievable compared to less than 100 $W/m^2$-K in non-fluidized heat transfer cases. The high thermal mass or heat capacity of the catalyst particles impinging the inner surface of the reactor wall of the fluidized bed reactor at a high frequency substantially improves heat transfer to the catalyst particles and gas flow inside the reactor. A uniform catalyst bed temperature is realized, which is attributable to large surface area of catalyst particles circulating within the reactor that are in contact with surrounding gas flow in a random manner.

Traditional heat supply through a fixed catalyst bed is highly limited as the catalyst in stationary position itself impedes heat transfer. As a result, steep temperature gradients develop across the catalyst bed. Excessively hot catalysts near the reactor wall are susceptible to catalyst deactivation and thermal degradation while catalysts located away from the reactor wall lack thermal energy and are unable to drive endothermic reactions.

FCC-style heat supply through coke burning in deactivated catalyst particles and circulation of the heated catalyst particles is not suitable for light alkane conversion because coke yield in light alkane conversion is too low to meet the reaction heat required for industrially attractive production rates. Light alkane dehydrogenation for aromatic hydrocarbon production requires much larger reaction heats than scission of carbon-carbon bond in cracking of heavy portions of crude oil in an externally circulating fluidization system. Compared to 5 mole % or higher coke yield obtainable in catalytic cracking of heavy portions of crude oil in an externally circulating fluidization system, light alkane conversion to aromatic hydrocarbons produces less than 1 mole % of coke yield. This low yield of coke cannot provide sufficient reaction heat through coke burning for industrially attractive conversion rates in an externally circulating fluidization system. Burning additional fuel in order to raise catalyst particles temperature would lead to an undesirable increase of heavy aromatics production and loss in catalyst performance and mechanical strength of the catalyst.

The reactor wall material of the present invention is comprised of alloy metals that exhibit high thermal conductivity. Thermal conductivities higher than 20 W/m-K of the alloy metals have proven effective for heat transfer in high temperature chemical processes such as steam crackers for olefins production and steam methane reformers for synthesis gas production. Heat flux higher than 40 $kW/m^2$ is achievable through the reactor wall made of the alloy metals.

Catalyst bed temperatures are preferably maintained between 500° C. and 660° C., more preferably between 520° C. and 640° C., and most preferably between 540° C. and 620° C. for aromatic hydrocarbons production. Above 660° C., catalyst deactivation driven by coking progresses rapidly and shortens the cycle time between catalyst regeneration. Below 500° C., the aromatic hydrocarbons production rate is too low to meet industrially attractive production rates. The reactor pressure is 200 psig (1,480 kPa) or less, preferably between 30 psig (308 kPa) and 90 psig (722 kPa).

The present invention provides an effective supply of thermal energy to the reactors while achieving a uniform catalyst bed temperature inside the reactors, and is in part enabled by using fluidized bed reactors. Catalyst particles are fluidized, internally circulated inside the reactor, and driven by upward flow of feedstock. The fluidized bed reactors may be fully or partially located inside or surrounded by a furnace where the flue gas from combustion of gaseous or liquid fuel provides thermal energy through the exterior of the reactor or the reactor wall to the catalyst particles and gas flow inside the reactor.

Figure 4:
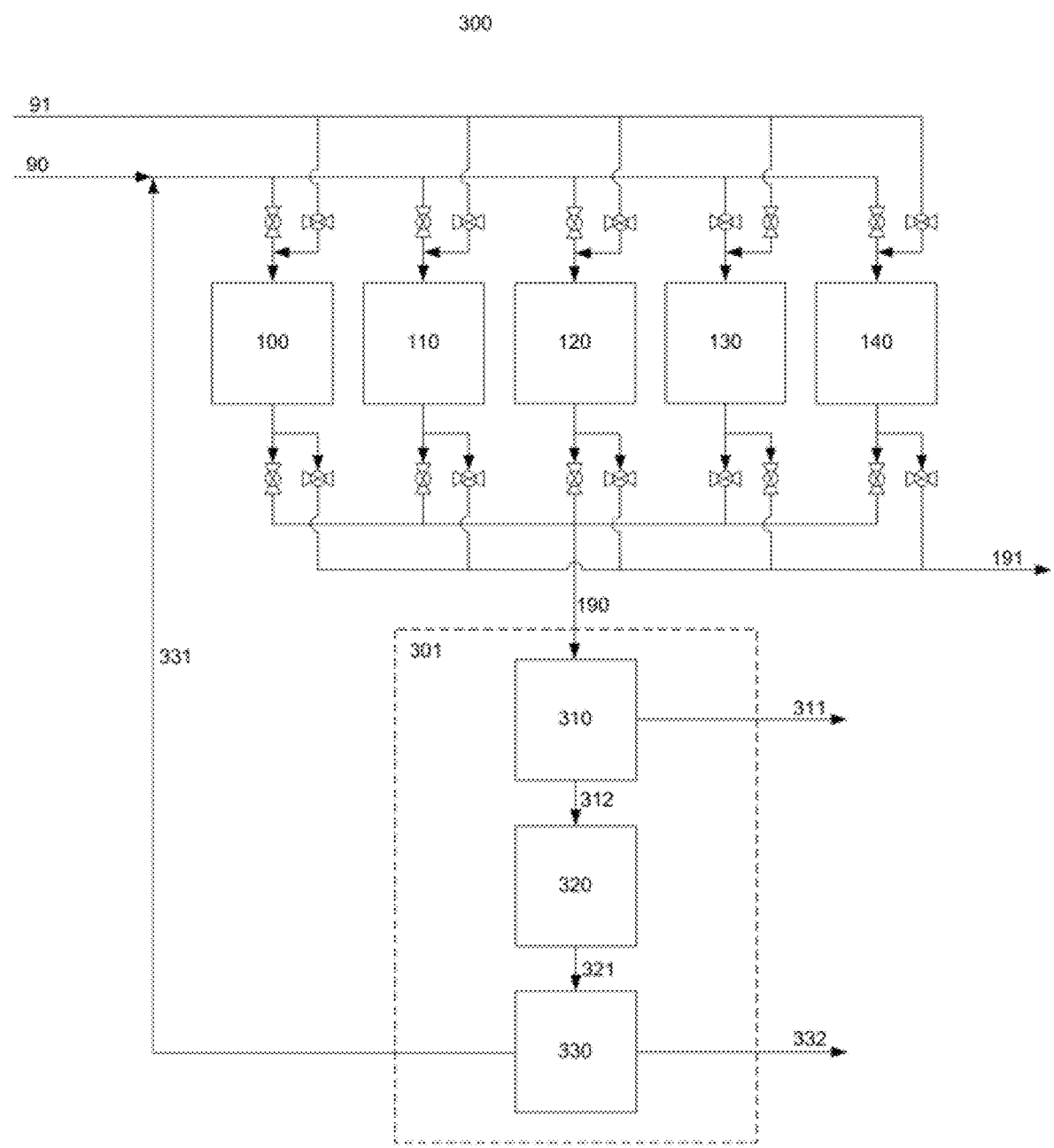
FIG. 4 is a simplified schematic diagram of the present invention in which product streams of reactors from multiple furnaces are integrated with a downstream separation system for separation of aromatic hydrocarbons and recycling of unreacted alkanes and alkenes to the reactors, while a group of reactors in the other furnace is under catalyst regeneration mode operation.

FIG. 4 shows a simplified schematic diagram of the present invention in which product streams comprising aromatic hydrocarbons from multiple furnaces are integrated with downstream separation system for separation of aromatic hydrocarbons, and recycling of unreacted alkanes and alkenes to the reactors. An integrated production system 300 comprises multiple furnaces (100, 110, 120, 130 and 140), and separation system 301. The number of furnaces is determined based on overall production rate target, the number of reactors inside a furnace, and the production rates of individual reactors.

The fluidized bed reactors in a furnace may be switched between in a production mode for producing aromatic hydrocarbons and in a regeneration mode for regenerating catalysts deactivated during the production mode. As an example, reactors in furnace 100, 110, 120, and 140 are in a production mode of aromatic hydrocarbons, while reactors in furnace 130 are in a catalyst regeneration mode. The reactors inside the furnace 130 are fluidly disconnected from the reactors in the other furnaces by closing valves for the light alkane feed supply and from the merged reactor effluent connection to separation system 301. The gas stream for catalyst regeneration 91, which includes either air or hydrogen, enters the reactors in furnace 130 for catalyst regeneration. The resultant catalyst regeneration effluent 191 is removed out of the system. Reactors in a furnace are transitioned as a group between the production mode and the regeneration mode in an orderly manner. Integration of multiple furnaces with the capability of switching operations between in the production mode and in the regeneration mode realizes continuous production of aromatic hydrocarbons without disrupting operation of the downstream separation system 301.

First merged effluent streams from the furnaces in the production mode are combined to form a second merged effluent stream 190. A liquid product 311, which comprises aromatic hydrocarbons, is separated from the second merged effluent stream 190 as it passes through a vapor-liquid separator 310. The vapor-liquid separator is also referred as "flash drum," "knock-out drum," or "knock-out pot." A gaseous product 312, which comprises hydrogen, methane, and $C_2$-$C_4$ range hydrocarbons, goes through a compressor 320 for an elevated pressure to become a compressed gaseous product 321 before entering a de-methanizer 330. The de-methanizer 330 is a low-temperature process and is used to separate methane from natural gas liquids such as ethane, propane and butane. Light hydrocarbons 331, comprised of $C_2$-$C_4$ alkanes and alkenes, are separated by the de-methanizer 330 and may be recycled to the reactors of aromatic hydrocarbons production mode operation after being merged with light alkane supply 90. Light alkane supply 90 may come from light alkane pipeline or other sources. Fuel gas 332, mainly comprising methane and hydrogen, may be used for process energy requirement including flue gas production inside the furnaces.

The invention claimed is:

1. A method for producing aromatic hydrocarbons comprising:
providing a plurality of reactors arranged in parallel with each other in a furnace, wherein each of the reactors is a fluidized bed reactor and comprises catalyst particles;
splitting a light alkane feed into multiple feed streams;
feeding each of the multiple feed streams to a corresponding reactor among the plurality of reactors;
converting at least a portion of each of the multiple feed streams to produce a reactor effluent stream containing aromatic hydrocarbons converted from the light alkane feed using the catalyst particles;
merging reactor effluent streams from the plurality of reactors to form a first merged effluent stream;
separating the first merged effluent stream into the aromatic hydrocarbons, light hydrocarbons, and a fuel gas; and
regenerating the catalyst particles to reactivate the catalyst particles deactivated during the converting step,
wherein all the reactors in the furnace are switched as a group between in a production mode for performing the converting step and in a regeneration mode for regenerating the catalyst particles deactivated during the converting step,
wherein a top end portion of each of the reactors is protruded from a top surface of the furnace and the protruded portion is up to 70% of a length of each of the reactors in a height direction, and
wherein, during the converting step, the catalyst particles reach a level of the top surface of the furnace.

2. The method of claim 1, wherein the light alkane feed comprises ethane, propane, butane, or a combination thereof.

3. The method of claim 1, wherein the fuel gas comprises methane and hydrogen.

4. The method of claim 1, wherein the light hydrocarbons comprise alkanes and alkenes from $C_2$ to $C_4$.

5. The method of claim 1, wherein the catalyst particles are fluidized and circulated in each of the reactors.

6. The method of claim 1, wherein the catalyst particles are 10-500 micrometers in diameter.

7. The method of claim 1, wherein, in the converting step, an outside wall of each of the reactors is heated by a flue gas, wherein the flue gas is generated by combustion of a gaseous fuel or a liquid fuel.

8. The method of claim 1, wherein a pressure of each of the reactors is 200 psig (1,480 kPa) or less during the converting step.

9. The method of claim 1, wherein a temperature of the catalyst particles is between 500° C. and 660° C. during the converting step.

10. The method of claim 1, wherein a temperature of the furnace is between 700° C. and 1200° C. during the converting step.

11. The method of claim 1, wherein the furnace comprises multiple furnaces and the first merged effluent stream from each of the multiple furnaces is further merged with each other to form a second merged effluent stream.

12. The method of claim 11, wherein all the reactors in the furnace in which the regenerating step occurs are fluidly disconnected from the light alkane feed and fed with a gas stream containing either air or hydrogen during the regenerating step.

13. The method of claim 12, wherein all the reactors in the furnace in which the regenerating step occurs are fluidly disconnected from the second merged effluent stream.

* * * * *